United States Patent [19]

Lefevre et al.

[11] Patent Number: 5,773,604

[45] Date of Patent: Jun. 30, 1998

[54] POLYOL COMPOSITION, PROCESS FOR ITS PREPARATION AND ITS APPLICATIONS

[75] Inventors: Philippe Lefevre, Merville; Jean-Paul Salome, Vieux-Berquin, both of France

[73] Assignee: Roquette Freres, Lestrem, France

[21] Appl. No.: 467,320

[22] Filed: Jun. 6, 1995

[30] Foreign Application Priority Data

Nov. 10, 1994 [FR] France .................................. 94 13583

[51] Int. Cl.$^6$ .......................... C08B 37/00; C08B 31/00; C07H 1/00
[52] U.S. Cl. ....................... 536/104; 536/102; 536/123.1; 536/123.13; 536/124; 568/852
[58] Field of Search ........................... 568/852; 536/1.11, 536/56, 102, 123.1, 124, 123.13, 104

[56] References Cited

U.S. PATENT DOCUMENTS 3,935,071  1/1976  Bergmeyer et al. .................... 435/137

FOREIGN PATENT DOCUMENTS 0 168 315  1/1986  European Pat. Off. .
2 054 829  5/1971  France .
2177931    3/1973  France .

OTHER PUBLICATIONS

"Chemical conversion of starch based glucose syrups", ch. 9, pp. 278–281 of Starch Conversion Technology, 1985, vol. 14, by A.P.G. Kieboom and H. Van Bekkum.

Primary Examiner—John Kight
Assistant Examiner—Everett White
Attorney, Agent, or Firm—Larson & Taylor

[57] ABSTRACT

The invention relates to a polyol composition exhibiting a very high heat stability and a very high chemical stability, characterized in that it exhibits an optical density lower than or equal to 0.100 in an S test. The invention also relates to a process for the preparation of such a composition, this process consisting in subjecting a polyol syrup to a stabilization stage such as a fermentation, an oxidation or a caramelization, and then to a purification stage. The invention also relates to the application of this composition to the manufacture of products using alkalis or undergoing a heat treatment at high temperature.

12 Claims, No Drawings

POLYOL COMPOSITION, PROCESS FOR ITS PREPARATION AND ITS APPLICATIONS

The present invention relates to a polyol composition exhibiting a very high heat stability and a very high chemical stability in alkaline medium. It also relates to a process for the preparation of this composition and to its applications.

In the present invention the term polyols denotes the products obtained by catalytic hydrogenation of simple reducing sugars, as well as more complex reducing sugars composed of the higher homologues of these simple sugars, such as disaccharides, oligosaccharides and polysaccharides and mixtures thereof.

In general, the simple reducing sugars which are intended for the catalytic hydrogenation in order to obtain polyol compositions of the type of those of the invention are glucose, xylose, fructose and mannose. The polyols obtained are then sorbitol, xylitol and mannitol.

The disaccharides are in most cases maltose, isomaltulose, maltulose, isomaltose and lactose, which, by hydrogenation, produce maltitol, isomalt, isomaltitol and lactitol.

Oligosaccharides and polysaccharides, which are products of increasingly high molecular weight usually originate from an acidic and/or enzymatic hydrolysis of starches and/or tuber starches, of xylans or of fructans like inulin, but can also be obtained by acidic and/or enzymatic recombination of mono- or disaccharides such as those referred to above.

Polyol composition is intended in the present invention to mean mixtures of polyols which form syrups that are uncrystallizable at 20° C. and have a solids content of 70% when they are kept in an airtight container during one month's storage. Some of these syrups can even form organic glasses, like boiled sugars, which resist crystallization.

The confectionary, pharmaceutical and oral and dental hygiene industries and even chemical industries commonly employ polyol compositions in the manufacture, for example, of sugar-free boiled sweets, of antacid or cough syrups, of toothpastes or polyurethane foams.

The sorbitol syrups obtained by hydrogenation of glucose or of starch hydrolysates of variable but high richness in glucose represent a very important class because of their economic weight. These syrups are employed above all as products replacing sugars. Their sugary taste makes it possible to prepare numerous low-calorie and weakly cariogenic products such as certain confectionery or such as certain pharmaceutical syrups.

Sorbitol syrups are employed secondly because of their outstanding moisturizing power. Thus, in the case of the manufacture of toothpastes, of cosmetic creams and milks, of shaving foams, as well as of foodstuffs such as pastries made with sweetened dough and cakes and of other products such as tobacco or paper. In these fields, sorbitol syrups or rather polyol compositions which are not crystallizable or difficult to crystallize are preferably employed because it is the property of moisturization, which is only imparted in the dissolved state, that is sought after.

Thirdly, other uses of sorbitol syrups exploit the plasticizing properties of sorbitol. This is the case in the industry of adhesives, of biodegradable plastics and also in the chewing gum industry.

In the fourth place, finally, sorbitol syrups are sometimes employed as chemical intermediates in the manufacture, for example, of sorbitan esters or of initiator for the manufacture of polyurethane foams and of alkyd resins. In this case it is the chemical properties of the polyols that are called into use.

Maltitol syrups, obtained by catalytic hydrogenation of hydrolysates of starch of variable richness in maltose, also represent an important class among the polyol compositions. Today they are essentially employed because of their high sweetening power, in order to prepare, as with the aid of sorbitol syrups, noncariogenic food and pharmaceutical products. It has been envisaged to employ them also as chemical intermediates for preparing surfactants and forming part of the composition of polyurethane foams.

Xylitol syrups, representing a third class of the polyol compositions, are today products which are in full development. Although they are more costly than sorbitol or maltitol syrups, there are plans to employ them in the same applications as those referred to above, especially because of their very high sweetening power and their outstanding moisturizing properties.

Industry also employs other polyol compositions. Hydrogenated glucose syrups which are rich in oligo- and polysaccharides thus find application in the foundry field, in quenching metals or in detergency.

Other syrups based on hydrogenated oligo- and polysaccharides, obtained by acidic and/or enzymatic recombination of glucose and of maltose in particular, begin to be employed in industry. They are, for example, hydrogenated polydextrose, of which it is commonly thought that it could be advantageously employed in the food industry as a very low-calorie filler, in particular in the manufacture of beverages, of iced products and of confectionery.

It is known that the applications of polyol compositions are, however, limited in some industrial sectors by the fact that these compositions do not fully satisfy the constraints of heat stability and of stability in alkaline medium.

Thus, a phenomenon of yellowing of these compositions at high temperature is observed when they are employed in the manufacture of boiled sugars. Such a colouring is often incompatible with some flavourings in sweets.

In the manufacture of alkaline toothpastes, pastes in which the abrasive agent consists of sodium bicarbonate crystals, it is preferred to employ other products—albeit less economical than the polyol compositions—such as glycols, propanediols or glycerine, because polyol compositions take on a brown colour in the course of time in these products.

In the manufacture of certain quality tobaccos it is also preferred to employ glycerine because of the interfering tastes which the polyol compositions impart, even though their moisturizing properties may be considered to be superior.

It also happens that these polyol compositions are set aside from the manufacture of surfactants, of polyurethane foams, of washing powders, of detergents and of antacid pharmaceutical syrups because of the yellowish or even brown colour which they impart to these products although, here too, they satisfy all the other technical constraints relating to these applications.

There is therefore at the present time a need to have available polyol compositions which are thermally and chemically more stable than those available on the market.

Now, it is to the credit of the Applicant Company to have discovered that polyol compositions exhibit satisfactory stability conditions as soon as their optical density, measured in an S test, is lower than or equal to 0.100.

The S test relies on a spectrophotometric measurement applied to the products to be tested.

To conduct this S test the procedure is as follows:
  the polyol syrup to be tested is brought to a solids content of 40% by weight, if need be by concentration or by aqueous dilution, to 5 ml of this solution are added 500 mg of sodium hydrogencarbonate of ultrapure quality, sold, for example, under the name RP Normapur™, analytical grade, by the company Prolabo, 65 Bd Richard Lenoir, Paris, France, and 250 mg of an aqueous solution containing 20% of ammonia, the whole is mixed and heated for 2 hours on a steam bath at 100° C. without stirring being applied, the solution is brought to 20° C. and the optical density of the solution thus obtained is measured at a wavelength of 420 nm by virtue of a spectrophotometer such as that marketed by Perkin-Elmer under the trademark Lambda 5 UV/VIS Spectrophotometer. By virtue of this apparatus, to give an example, optical densities of 0.040, 0.080 and 0.120 are obtained by replacing 5 ml of polyol solution with a solids content of 40% with 5 ml of a solution containing 40, 80 and 120 parts per million, respectively, of anhydrous D-glucose RP Normapur™, analytical grade, (Prolabo), dissolved in distilled water.

The polyol composition is proportionally more stable the lower the value measured in the S test.

As the Applicant has verified, it should be noted that, surprisingly and unexpectedly, there seems to be no correspondence between, on the one hand, the richness of polyol compositions in any particular polyol, or else their content of residual or free reducing sugars (measured by the usual Bertrand sodium copper tartrate method or the method using dinitrosalicylic acid) and, on the other hand, the result obtained in the S test.

In other words, no direct relation appears to exist between the thermal and chemical stability of a polyol composition and its residual reducing sugar content.

This could be explained by the fact that the S test yields an overall measurement and that the colour obtained in this test depends probably all at the same time on the final pH of the syrup, on the quantity of inorganics present within the syrup, on the nature of these inorganics, on the quantity of reducing functional groups not reduced by the hydrogenation and on the nature of the molecules carrying these unreduced functional groups: monosaccharides, disaccharides, oligo- or polysaccharides.

Thus, for example, in the S test it is observed that, surprisingly, traces of unreduced oligo- and polysaccharides give rise, everything else being otherwise the same, to more intense colours than do the unreduced mono- and disaccharides, at the same concentration of reducing functional groups.

Thus, 180 parts per million (ppm) of dextrose are less liable to colouring in basic medium than 342 ppm of maltose expressing the same reducing power, which themselves colour less than higher concentrations of oligosaccharides or of polysaccharides expressing the same reducing power.

Such a finding leads to the thought that, in order to obtain polyol compositions in accordance with the invention—especially when they contain a large quantity of reduced oligo- and polysaccharides—it would be necessary and sufficient to continue the catalytic hydrogenation longer than is customary, so as to obtain residual or free reducing sugar contents at the limit of detection by analysis.

Catalytic hydrogenation of glucose or of glucose syrups, as well as that of fructose or of xylose, as currently practiced, is described, for example, in "Chemical conversion of starch based glucose syrups", ch. 9, pages 278–281, of Food and Sci. Technol., 1985, vol. 14 by A. P. G. Kieboom and H. van Bekkum.

However, the Applicant Company has observed that, on the one hand, it is not necessary to lengthen the catalytic hydrogenation unreasonably in order to obtain the composition according to the invention and that, on the other hand, such a lengthening of the hydrogenation does not make it possible to obtain the said composition.

It appears, in fact, that di-, oligo- and polysaccharides are more difficult to hydrogenate completely than monosaccharides.

Following numerous investigations, the Applicant has found that, in order to obtain the compositions in accordance with the invention it is appropriate to add at least one additional so-called "stabilization" stage to the conventional catalytic hydrogenation processes. This stabilization stage may consist, for example and without this constituting a limitation, of a fermentation, oxidation or caramelization stage.

The stabilization stage makes it possible to obtain a polyol composition exhibiting an optical density lower than or equal to 0.100 in the S test. This stage must be placed after the hydrogenation stage and preferably before the final stage of purification of the polyol composition.

The invention relates therefore firstly to a polyol composition characterized in that it exhibits an optical density lower than or equal to 0.100 in the S test. The polyol composition according to the invention exhibiting an optical density lower than or equal to 0.100 in the S test preferably includes, in relation to its polyol content in the dry state, a content of 0.01 to 95% of hydrogenated monosaccharides and/or of hydrogenated disaccharides, the remainder to 100% of the polyols consisting of hydrogenated oligo- and polysaccharides these contents being expressed in relation to the solids content of polyols present.

The hydrogenated monosaccharides may be advantageously chosen from the group including sorbitol, iditol, mannitol, xylitol, arabitol and erythritol and more preferably from sorbitol, mannitol and xylitol.

The hydrogenated disaccharides may be advantageously chosen from the group including maltitol, hydrogenated maltulose, hydrogenated isomaltulose or isomalt (mixture of 1,6-glucopyranosidomannitol and of 1,6-glucopyranosidosorbitol), isomaltitol, lactitol, hydrogenate inulobiose and more preferably from maltitol, lactitol and hydrogenated isomaltulose.

The hydrogenated oligosaccharides and polysaccharides may consist of maltotriitol, maltotetraitol and other hydrogenated oligo- and polysaccharides obtained by hydrolysis of starch, followed by a hydrogenation. The said hydrogenated oligosaccharides and polysaccharides may, however, also consist of cellobiitol, cellotriitol, xylobiitol, xylotriitol and other hydrogenated oligo- and polysaccharides obtained by hydrolysis, generally acidic, of cellulose, of xylans, of fructans like, for example, inulin, dextrins, polyglucoses such as polydextrose, followed by a hydrogenation. The said hydrogenated oligo- and polysaccharides may also originate from an acidic or enzymatic recombination of optionally reduced mono- or disaccharides such as those referred to above, by themselves or in the presence of other optionally reduced oligo- and polysaccharides, followed by a hydrogenation. The hydrogenated oligosaccharides and polysaccharides which it is preferred to see present within the composition are the oligo- and polysaccharides originating from hydrogenated hydrolysates of starch, of dextrins and hydrogenated polyglucoses, optionally previously hydrolysed.

The content of mono- and disaccharides in the polyol composition in accordance with the invention is more preferably between 0.1 and 90%, still more preferably between 0.5 and 86% and still better between 50 and 86% of the polyols, the said contents being expressed in relation to the solids content of the polyols present in the composition; the content of hydrogenated oligo- and polysaccharides representing the remainder to 100% of this solids content. It is thus that it is possible advantageously to obtain, for some applications, a composition which is less liable to the crystallization of any one of these hydrogenated mono- or disaccharides.

In order to be as suitable as possible for uses where constraints in terms of taste and of thermal or chemical stability are the most draconian, the polyol composition in accordance with the invention preferably exhibits an optical density lower than or equal to 0.075, more preferably lower than or equal to 0.060 and, better still, lower than or equal to 0.040 in the S test. It may be noted here that these optical density values, which characterize the polyol composition in accordance with the invention are very markedly lower than the values found for polyol compositions described or marketed hitherto. In fact, in the case of these latter products the optical density in the same S test is always much higher than 0.100 and generally between 0.500 and 0.850.

According to whether it is more or less rich in mono- and disaccharides, the polyol composition in accordance with the invention exhibits a total sugar content, after total hydrolysis according to the Bertrand method, of between 3.5 and 98%, preferably between 6 and 92% and still more preferably between 8 and 90%, this content being expressed in relation to the solids content of the composition.

The polyol composition in accordance with the invention may be presented in the form of syrup or powder, depending on the subsequent destination for which it is intended. Bearing in mind its very great stability and its high compatibility with the very great majority of the ingredients or additives employed in industry, it can also be mixed with the most diverse products. In particular, glycols like ethylene glycol, propylene glycol, dipropylene glycol, diethylene glycol and polyethylene glycols, glycerine or propanediols may be added without any disadvantage to the composition of the invention in order to adjust the functional properties of the composition to present it under the form of a syrup with a very high dry matter content, i.e. up to 96% of dry matter.

The invention relates secondly to a process for the preparation of a stable polyol composition.

This process is characterized in that a syrup of polyols obtained by catalytic hydrogenation of simple or complex reducing sugars is subjected to the sequence of the following stages:

a stabilization stage such as a fermentation, an oxidation or a caramelization, aimed at bringing the optical density of the hydrogenated syrup to a value lower than or equal to 0.100, preferably lower than or equal to 0.075 and still more preferably lower than or equal to 0.060 in the S test, a stage of purification of the "stabilized" hydrogenated syrup thus obtained.

It is obvious that the process in accordance with the invention may include other stages which are conven- tional and known to a person skilled in the art, like in particular stages of purification on earths, active carbon and/or resins, of concentration and of optional drying.

The stabilization stage is preferably performed on a demineralized hydrogenated syrup in order to remove all traces of soluble nickel or of other hydrogenation catalysts.

It is preferred to subject to the process in accordance with the invention a polyol syrup obtained by catalytic hydrogenation of simple or complex reducing sugars until a percentage of residual reducing sugars lower than 0.50% as measured by the Bertrand method is obtained. This percentage is more preferably lower than 0.25% and still more preferably lower than 0.20%.

It is also preferred to employ a demineralized polyol syrup, especially in the case where the stabilization stage consists in a ferment treatment or enzymatic oxidation.

It is thus preferred to employ as product intended for the stabilization stage—though without this being essential, however—a polyol syrup exhibiting an optical density preferably lower than or equal to 0.200, more preferably lower than or equal to 0.170 and still more preferably lower than or equal to 0.150 in the S test.

According to a first possibility the stabilization stage consists of a stage of enzymatic oxidation with the use of a glucose oxidase. This enzymatic oxidation is preferably performed in the presence of catalase.

The glucose oxidase catalyses the following reaction:

$$glucose + O_2 + H_2O \rightarrow gluconic\ acid + H_2O_2$$

The catalase converts the aqueous hydrogen peroxide thus produced, according to the reaction:

$$H_2O_2 \rightarrow H_2O + \tfrac{1}{2}O_2$$

Such an enzyme composition is available, for example, from the Novo company, Denmark, under the name SP 358.

This enzymatic oxidation must take place in an aerated medium and the pH of the medium is maintained at a value of between 3.5 and 8.0, preferably between 4.0 and 7.0 and still more preferably between 5.0 and 6.0.

The concentration of the hydrogenated, preferably demineralized, syrup is not critical and may vary from 5 to 75%. However, high concentrations may make it necessary to work while controlling the pH with the aid of a base or while performing the oxidation in the presence of a buffer salt such as calcium carbonate. Stabilization of the pH at a value of between 5.0 and 6.0 is preferable.

For economic reasons, however, it is preferred to perform the oxidation on aqueous solutions with a solids content of approximately 30 to 50%. The temperature may be adjusted within a wide range varying from 15° to 70° C. but, for reasons of convenience, it is preferred to work at about 30°–40° C., at which temperatures the enzyme is found to be most active.

A convenient equipment enabling this oxidation to be performed consists of an aerobic fermenter, although it is not necessary at all for this stage to take place in sterile or even strictly aseptic conditions. The quantity of enzymes used is such that the oxidation takes place in 0.5 to 24 hours.

This enzymatic oxidation stage, in the presence or absence of catalase, must be followed by a stage of demineralization on an anion exchanger in OH- hydroxyl form, so as to remove the acids formed by the action of the enzyme.

As anion exchanger it is preferred to employ a strong anionic resin which makes it possible to bind efficiently both the weak acids such as gluconic acid or of other acids from glucose oxidation which may have appeared, and the acids sometimes present inherently in the hydrogenated product, like citric acid in the case of hydrogenated polydextrose.

The preferred resins are those which carry functional groups of the quaternary amine type and preferably quaternary trimethylamine groups, such as the Amberlite IRA 900 resin marketed by Rohm and Haas.

These resins are employed in their OH- hydroxyl or strong base form.

To increase their efficiency of regeneration with alkalis, it may be preferred to couple them with a weak anionic resin essentially carrying tertiary amine groups, such as Amberlite IRA 93 from the same company.

According to a second possibility the stabilization stage consists of a stage of chemical oxidation. This chemical oxidation is preferably performed in the presence of methylene blue, of hydroquinone or of resorcin, so as to catalyse the reactions and to increase the oxidation yields. The procedure may be a known one in the case of reducing sugar syrups, for example by following the Spengler—Pfannenstiel process described in the paper by Dubourg and Naffa (Bull. Soc. chim. Fr. (1959) 1353–1362). After oxidation the syrup must be purified according to the same techniques as those described above for the enzymatic oxidation.

According to a third possibility the stabilization stage is a ferment stage. Use is then made of the ability of some microorganisms, for example some yeasts, of metabolizing simple sugars and not the polyols and of con- verting them, for example, into ethanol and carbon dioxide. To do this, it is appropriate to add to the syrup a source of nitrogen such as, for example, yeast extracts. It is obvious that the fermentation conditions must be adjusted as a function of the type of microorganism chosen.

However, it is preferred to adopt microorganisms which are at the same time osmophilic and thermophilic, so as to have the ability, for cost reasons, of working at high solids content and at an elevated temperature.

With a view to facilitating the subsequent purification, it is also preferred to choose microorganisms which do not produce secondary metabolites. Carbon dioxide alone or organic acids are then produced.

After fermentation it is appropriate to eliminate the biomass produced, for example by sedimentation, centrifuging or filtration, before purifying the polyol syrup further. Heating to about 80° C. enables ethanol which may be produced to be removed, while a treatment on anion exchange resins is found to be useful for removing the acids which may have formed during the fermentation.

According to a fourth and final method, the stabilization stage consists of a stage of alkaline degradation or a caramelization stage.

It is preferred to work at an alkaline pH of between 8 and 12 and preferably with heating, so as to shorten the reaction times. The products of caramelization, consisting essentially of acids, may be removed by passing over resins.

The process in accordance with the invention makes it possible to obtain polyol compositions of a thermal and chemical stability unequalled hitherto, and to do so at an acceptable cost.

In all cases, of course, the organoleptic properties and the residual colour of the products obtained can be improved further by additional treatments, for example with the aid of animal or vegetable black.

One of the main merits of the present invention is that of providing a polyol composition which is very stable and which does not generate undesirable flavours or colours in very diverse conditions of application. In the third place, therefore, the invention relates to the use of the said polyol composition. This composition may be employed as a sweetening agent, texturing agent, complexing agent, moisturizing agent or plasticizing agent, in a large number of products. Bearing in mind its complete compatibility with a large number of ingredients and additives usually employed in industry, it may be advantageously used in combination or mixed with stabilizers, emulsifiers, flavourings, sugars, intense sweeteners, bases, pharmaceutical or veterinary active substances, fatty substances, inorganic or organic filling agents such as polydextroses, fibres, fructo-oligosaccharides, gums, organic or inorganic gelling agents such as proteins, pectins, modified celluloses, extracts of algae and of seeds, bacterial polysaccharides and silicas.

The polyol composition in accordance with the invention can be suitable for the preparation of products intended to be ingested by man or animals, and can also form part of the formulation of products for hair care or for application to the skin. It can also be used in the detergents, tobacco or plastics industry. These products in which the polyol composition can be used may have a liquid or viscous texture; this is the case, for example, with beverages, syrups, emulsions, suspensions, elixirs, mouthwashes, drinkable phials and dishwashing liquids. They can also have a pasty texture, like antacid products or uncrystallized or semicrystallized confectionery products such as sweets, jellies, gums, chews, caramels, chewing gums, fillings and cereal bars. They can also have a gelled texture, as is the case with edible gels such as flans, jams, jellies, milk desserts, pharmaceutical and veterinary gels or toothpastes. Finally, they can have a solid texture, as in patisserie, biscuit manufacture and bakery products, tablets, side dishes, sprayed or extruded sweetening or flavouring powders, freeze-dried pharmaceutical or veterinary products, tobaccos and washing or dishwashing powders.

The composition in accordance with the invention is particularly recommended for preparing all kinds of products manufactured in the presence of alkalis, such as polyurethane foams, or containing alkaline agents, such as antacids, detergents, shaving foams, depilatory creams, and toothpastes based for example on sodium bicarbonate. It is also specially recommended for preparing products which are processed or obtained at very high temperature. This is the case, for example, with boiled sugars.

Another advantage of the polyol composition according to the invention is that it is particularly stable towards microorganism enzymes.

The examples which follow, and which are given without any limitation being implied, will provide a better illustration of the invention.

EXAMPLE 1

A polyol composition in accordance with the invention is prepared from a sorbitol syrup marketed by the Applicant under the trade name Neosorb 70/70. In the S test this syrup exhibits an optical density close to 0.600.

This syrup is adjusted to a solids content of 40% by dilution. The solution obtained is subjected to the action of glucose oxidase in a proportion of 70 GOX units of glucose oxidase SP 358 per kilogram of dry substrate. This reaction takes place in a tank aerated at a rate of 1.5 volumes of air per volume of solution per minute, at a pH controlled at 5.0 by gradual addition of sodium hydroxide.

It takes place at 35° C. for 16 hours, after which the solution is processed on a battery of ion exchange resins comprising an IR 200 C strong cationic resin and then an IRA 900 strong anionic resin in series.

In these conditions a polyol composition exhibiting a very markedly lowered optical density, close to 0.070, is obtained.

EXAMPLE 2

Toothpastes according to the following formulation are prepared:

| | |
|---|---|
| sodium bicarbonate | 30.0% |
| polyol composition (70% SC) | 36.0% |
| abrasive silica | 8.0% |
| thickening silica | 5.0% |
| carboxymethyl cellulose | 0.7% |
| sodium lauryl sulphate | 1.7% |
| methylparaben | 0.1% |
| titanium oxide | 0.7% |
| water | 17.8% |

A first toothpaste is manufactured by using, as polyol composition, the Neosorb 70/70 sorbitol syrup mentioned in Example 1 (control toothpaste).

A second toothpaste is prepared by employing the polyol composition according to the invention described in Example 1.

The toothpastes packaged in tubes of Polyfoil® type are stored for 10 days at 45° C. which corresponds to a storage period of approximately 15 months at 20° C.

At the end of this period it is found that the control toothpaste, initially white in colour, exhibits a light brown colour.

On the other hand, the toothpaste prepared from the polyol composition in accordance with the invention has an appearance which is unchanged when compared with the initial state. This constitutes a decisive technical and commercial advantage for the users.

EXAMPLE 3

The thermal stability of a sorbitol syrup of the prior art, marketed by the applicant under the trade name NEOSORB® 70/70, is compared with the thermal stability of a polyol composition according to the invention and obtained according to the method described in Example 1.

For this purpose, the two syrups, having a dry matter content close to 70%, are submitted, to a heating in an autoclave at 117° C. during 20 minutes.

Once the syrups have come back to room temperature, a blind testing is performed by a panel of 15 people.

It appears quite clearly that the polyol composition according to the invention is preferred due to its very neutral, less metallic taste, almost deprived of a caramel note. This property renders the polyol composition of the invention particularly interesting for numerous applications.

Moreover, a quite lower interference with some substances, and particularly with some aromas and intense sweeteners, has been observed.

Consequently, it is far easier to adjust the organoleptic quality of food products, tooth pastes, tobaccos and other products with the products according to the invention than with the syrups of the prior art.

We claim:

1. Polyol composition exhibiting an optical density lower than or equal to 0.100 in an S test.

2. Polyol composition according to claim 1, exhibiting an optical density lower than or equal to 0.075.

3. Polyol composition according to claim 2, exhibiting an optical density lower than 0.060.

4. Polyol composition according to claim 3, exhibiting an optical density lower than 0.040.

5. Polyol composition according to claim 1, having a total sugar content, after total hydrolysis according to the Bertrand method, of between 3.5 and 98%.

6. Polyol composition according to claim 5, having a total sugar content, after total hydrolysis according to the Bertrand method, of between 6 and 92%.

7. Polyol composition according to claim 6, having a total sugar content, after total hydrolysis according to the Bertrand method, of between 8 and 90%.

8. Polyol composition according to claim 1, including from 0.01 to 95% of hydrogenated mono- and/or disaccharides, the remainder to 100% consisting of hydrogenated oligo- and polysaccharides.

9. Polyol composition according to claim 8, wherein:

the hydrogenated monosaccharides are selected from the group consisting of sorbitol, mannitol and xylitol, and the hydrogenated disaccharides are selected from the group consisting of maltitol, lactitol and hydrogenated isomaltulose.

10. Process for the preparation of a stable polyol composition according to claim 1, wherein a syrup of polyols obtained by catalytic hydrogenation of simple or complex reducing sugars is subjected to the sequence of the following stages:

a stabilization stage, such as a fermentation, an oxidation or a caramelization, aimed at bringing the optical density of the hydrogenated syrup to a value lower than or equal to 0.100 in the S test, and a stage of purification of the stabilized hydrogenated syrup thus obtained.

11. Process according to claim 10, wherein the optical density of the hydrogenated syrup is brought to a value lower or equal to 0.075 in the S test.

12. Process according to claim 11, wherein the optical density of the hydrogenated syrup is brought to a value lower or equal to 0.060 in the S test.

* * * * *